US010858667B2

(12) United States Patent
Eckard et al.

(10) Patent No.: US 10,858,667 B2
(45) Date of Patent: Dec. 8, 2020

(54) PEPPER PLANTS WITH IMPROVED DISEASE RESISTANCE

(71) Applicant: Seminis Vegetable Seeds, Inc., St. Louis, MO (US)

(72) Inventors: Jonathan Tyler Eckard, St. Louis, MO (US); Patrick Hogan, St. Louis, MO (US); Carl Martin Jones, Sacramento, CA (US); Brian J. Just, Fort Myers, FL (US); Joel Kniskern, Sacramento, CA (US); Jae Hyoung You, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 15/836,610

(22) Filed: Dec. 8, 2017

(65) Prior Publication Data

US 2018/0171353 A1 Jun. 21, 2018

Related U.S. Application Data

(60) Provisional application No. 62/436,299, filed on Dec. 19, 2016.

(51) Int. Cl.
*C12N 15/82* (2006.01)
*A01H 6/82* (2018.01)
*A01H 5/08* (2018.01)

(52) U.S. Cl.
CPC .......... *C12N 15/8282* (2013.01); *A01H 5/08* (2013.01); *A01H 6/822* (2018.05); *C12N 15/821* (2013.01)

(58) Field of Classification Search
CPC ............................ C12N 15/8282; A01H 6/822
USPC ...................................................... 800/317.1
See application file for complete search history.

(56) References Cited

U.S. PATENT DOCUMENTS

| 8,962,944 B2* | 2/2015 | Just ............ A01H 5/08 435/430.1 |
| 9,974,258 B2 | 5/2018 | Vreugdenhil |
| 2012/0151622 A1 | 6/2012 | Moreau et al. |
| 2012/0159663 A1 | 6/2012 | McCarthy |
| 2013/0205419 A1* | 8/2013 | Just ............ A01H 5/08 800/260 |

FOREIGN PATENT DOCUMENTS

WO WO 2013/034747 3/2013

OTHER PUBLICATIONS

Lefebvre et al, "Both epistatic and additive effects of QTLs are involved in polygenic induced resistance to disease: a case study, the interaction pepper—Phytophthora capsici Leonian," Theor. Appl. Genet. 93:503-511, 1996.
Thabuis et al., "Comparative mapping of Phytophthora resistance loci in pepper germplasm: evidence for conserved resistance loci across Solanaceae and for a large genetic diversity," Theor. Appl. Genet. 106:1473-1485, 2003.
Thabuis et al., "Phenotypic and molecular evaluation of a recurrent selection program for a polygenic resistance to Phytophthora capsici in pepper," Theor. Appl. Genet. 109:342-351, 2004.
Thabuis et al., "Marker-assisted introgression of 4 Phytophthora capsici resistance QTL alleles into a bell pepper line: validation of additive and epistatic effects," Mol. Breeding 14:9-20, 2004.
Truong et al., "Identification of isolate-specific resistance QTLs to phytophthora root rot using an intraspecific recombinant inbred line population of pepper (Capsicum annuum)," Plant Pathology 61:48-56, 2012.
Truong et al., "Identification and development of molecular markers linked to Phytophthora root rot resistance in pepper (*Capsicum annuum* L.)," Eur. J. Plant Pathol. 135:289-297, 2013.
Liu et al., "Combined use of bulked segregant analysis and microarrays reveals SNP markers pinpointing a major QTL for resistance to Phytophthora capsici in pepper," Theor. Appl. Genet. 127:2503-2513, 2014.
Rehrig et al., "CaDMR1 cosegregates with QTL Pc5.1 for resistance to phytophthora capsici in pepper (Capsicum annuum)," The Plant Genome vol. 7 No. 2., 2014.
Mallard et al., "A key QTL cluster is conserved among accessions and exhibits broad-spectrum resistance to Phytophthora capsici: a valuable locus for pepper breeding," Mol. Breeding 32:349-364, 2013.
GenBank Accession No. HG975443, dated Nov. 19, 2015.
International Search Report and Written Opinion regarding International Application No. PCT/US2017/065140, dated Apr. 24, 2018.
U.S. Appl. No. 15/907,673, filed Feb. 28, 2018, Stoll.
U.S. Appl. No. 15/978,347, filed May 14, 2018, Stoll.
Larkin et al., "Somaclonal variation—a novel source of variability from cell cultures for plant improvement," *Theor Appl Genet*, 60(4):197-214; 1981.
Moose et al., "Molecular plant breeding as the foundation for 21st century crop improvement," *Plant Physiol*, 147(3):969-77, 2008.
Variety specific information as indicated in transmittal letter of Informational Disclosure Statement for U.S. Appl. No. 15/907,673, filed Jun. 7, 2018.

* cited by examiner

*Primary Examiner* — Li Zheng
(74) *Attorney, Agent, or Firm* — Dentons US LLP

(57) ABSTRACT

The present disclosure provides pepper plants exhibiting resistance to *Phytophthora capsici*. Such plants may comprise novel introgressed chromosomal regions associated with disease resistance. In certain aspects, compositions, including novel polymorphic markers and methods for producing, breeding, identifying, and selecting plants or germplasm with a disease resistance phenotype are provided.

28 Claims, 4 Drawing Sheets
Specification includes a Sequence Listing.

PEPPER PLANTS WITH IMPROVED DISEASE RESISTANCE

REFERENCE TO RELATED APPLICATION

This application claims the benefit of U.S. Provisional Application No. 62/436,299, filed on Dec. 19, 2016, which is incorporated herein by reference in its entirety.

FIELD OF THE INVENTION

The present invention relates to the field of agriculture and more specifically to methods and compositions for producing pepper plants exhibiting disease resistance and improved fruit quality.

INCORPORATION OF SEQUENCE LISTING

The sequence listing that is contained in the file named "SEMB023US_ST25.txt," which is 13 kilobytes as measured in Microsoft Windows operating system and was created on Dec. 7, 2017, is filed electronically herewith and incorporated herein by reference.

BACKGROUND OF THE INVENTION

Disease resistance is an important trait in agriculture, particularly for the production of food crops. Although disease resistance alleles have been identified in pepper plants, efforts to introduce these alleles into sweet pepper varieties have been hindered by the deleterious traits associated with the resistance alleles. The use of marker-assisted selection (MAS) in plant breeding methods has made it possible to select plants based on genetic markers linked to traits of interest such as disease resistance. However, accurate markers for identifying or tracking desirable traits in plants are frequently unavailable even if a gene associated with the trait has been characterized. These difficulties are further complicated by factors such as polygenic or quantitative inheritance, and an often incomplete understanding of the genetic background underlying expression of a desired phenotype. Therefore, in the absence of accurate and validated markers for use in MAS, it may not be feasible to produce new plant lines exhibiting certain disease resistance phenotypes.

SUMMARY OF THE INVENTION

In one aspect, the invention provides a pepper plant of a cultivated pepper variety comprising a recombinant introgression on chromosome 5 that comprises a first allele conferring resistance to *Phytophthora capsici*, and wherein said first allele lacks a second allele genetically linked thereto that confers a light green immature fruit color phenotype when present. In certain embodiments, the recombinant introgression is flanked in the genome of the plant by marker locus SNPmarker_7 (SEQ ID NO: 1) and marker locus SNPmarker_12 (SEQ ID NO: 6). In further embodiments, the recombinant introgression is located between about 39.4 cM and about 41.8 cM on chromosome 5 of the plant. In other embodiments, the recombinant introgression comprises the gene AIG1 on chromosome 5 of the plant. In additional embodiments, a sample of seed comprising the recombinant introgression was deposited under ATCC Accession No. PTA-123693. The invention further provides a plant part comprising the recombinant introgression provided herein. In certain embodiments, the plant part is a cell, a seed, a root, a stem, a leaf, a fruit, a flower, or pollen.

In another aspect, the invention provides a pepper plant of a cultivated pepper variety comprising a recombinant introgression on chromosome 5 that comprises a first allele conferring resistance to *Phytophthora capsici*, wherein said first allele lacks a second allele genetically linked thereto that confers a light green immature fruit color phenotype when present, and wherein the plant further comprises an introgressed chromosomal segment from chromosome 6 of a donor pepper plant, wherein said chromosomal segment confers improved *Phytophthora capsici* resistance under all disease pressures relative to a plant lacking said chromosomal segment. In certain embodiments, the chromosomal segment is associated with (selected by) marker locus SNPmarker_1 (SEQ ID NO: 8) or marker locus SNPmarker_2 (SEQ ID NO: 9). In further embodiments, the chromosomal segment is located between about 26.4 cM and about 28.7 cM on chromosome 6.

In another aspect, the invention provides a method for producing a pepper plant exhibiting resistance to *Phytophthora capsici* comprising: a) crossing a pepper plant of a cultivated pepper variety comprising a recombinant introgression on chromosome 5 that comprises a first allele conferring resistance to *Phytophthora capsici*, and wherein said first allele lacks a second allele genetically linked thereto that confers a light green immature fruit color phenotype when present with itself or with a second pepper plant of a different genotype to produce one or more progeny plants; and b) selecting a progeny plant comprising the recombinant introgression. In some embodiments, selecting a progeny plant comprises identifying a genetic marker genetically linked to said recombinant introgression. In particular embodiments, selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), and SNPmarker_21 (SEQ ID NO: 7). In other embodiments, selecting a progeny plant comprises detecting a polymorphism at locus SNPmarker_8 (SEQ ID NO: 2) and a polymorphism at locus SNPmarker_21 (SEQ ID NO: 7). In further embodiments, the progeny plant is an $F_2$-$F_6$ progeny plant. In selected embodiments, the producing of the progeny plant comprises backcrossing. In additional embodiments, the backcrossing comprises from 2-7 generations of backcrossing.

In another aspect, the invention provides methods for obtaining a pepper plant of a cultivated variety exhibiting resistance to *Phytophthora capsici* comprising: a) obtaining a pepper plant of a cultivated variety that is heterozygous for a first allele from a donor parent that confers resistance to *Phytophthora capsici* that is genetically linked to a second allele that confers a light green immature fruit color phenotype; b) obtaining progeny of the plant; and c) selecting at least a first progeny plant in which recombination has occurred such that the progeny comprises said first allele that confers resistance to *Phytophthora capsici* and lacks said second allele that confers a light green immature fruit color phenotype. In some embodiments, selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), and SNPmarker_21 (SEQ ID NO: 7). In additional embodiments, selecting a progeny plant further comprises detecting a polymorphism at locus SNPmarker_8 (SEQ ID NO: 2) and a polymorphism at locus SNPmarker_21 (SEQ ID NO: 7). In some further embodiments, the invention provides a plant produced by the methods provided herein or a part of said plant, such as a cell, a seed, a root, a stem, a leaf, a fruit, a flower, or pollen.

In another aspect, the invention provides methods for producing a pepper plant exhibiting improved *Phytophthora capsici* resistance under all disease pressures comprising: a) crossing a pepper plant of a cultivated pepper variety comprising a recombinant introgression on chromosome 5 that comprises a first allele conferring resistance to *Phytophthora capsici*, wherein said first allele lacks a second allele genetically linked thereto that confers a light green immature fruit color phenotype when present, and wherein the plant further comprises an introgressed chromosomal segment from chromosome 6 of a donor pepper plant, wherein said chromosomal segment confers improved *Phytophthora capsici* resistance under all disease pressures relative to a plant lacking said chromosomal segment with itself or with a second pepper plant of a different genotype to produce one or more progeny plants; and b) selecting a progeny plant comprising said recombinant introgression and said introgressed chromosomal segment. In some embodiments, selecting a progeny plant comprises 1) identifying a genetic marker genetically linked to said recombinant introgression; and 2) identifying a genetic marker genetically linked to said introgressed chromosomal segment. In further embodiments, selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), SNPmarker_21 (SEQ ID NO: 7), SNPmarker_1 (SEQ ID NO: 8), and SNPmarker_2 (SEQ ID NO: 9). In yet further embodiments, selecting a progeny plant comprises detecting a polymorphism at locus SNPmarker_8 (SEQ ID NO: 2), a polymorphism at locus SNPmarker_21 (SEQ ID NO: 7), a polymorphism at locus SNPmarker_1 (SEQ ID NO: 8), and a polymorphism at locus SNPmarker_2 (SEQ ID NO: 9). In some embodiments, the progeny plant is an $F_2$-$F_6$ progeny plant. In other embodiments, the producing of the progeny plant comprises backcrossing. In yet other embodiments, the backcrossing comprises from 2-7 generations of backcrossing.

DETAILED DESCRIPTION

Figure 1:
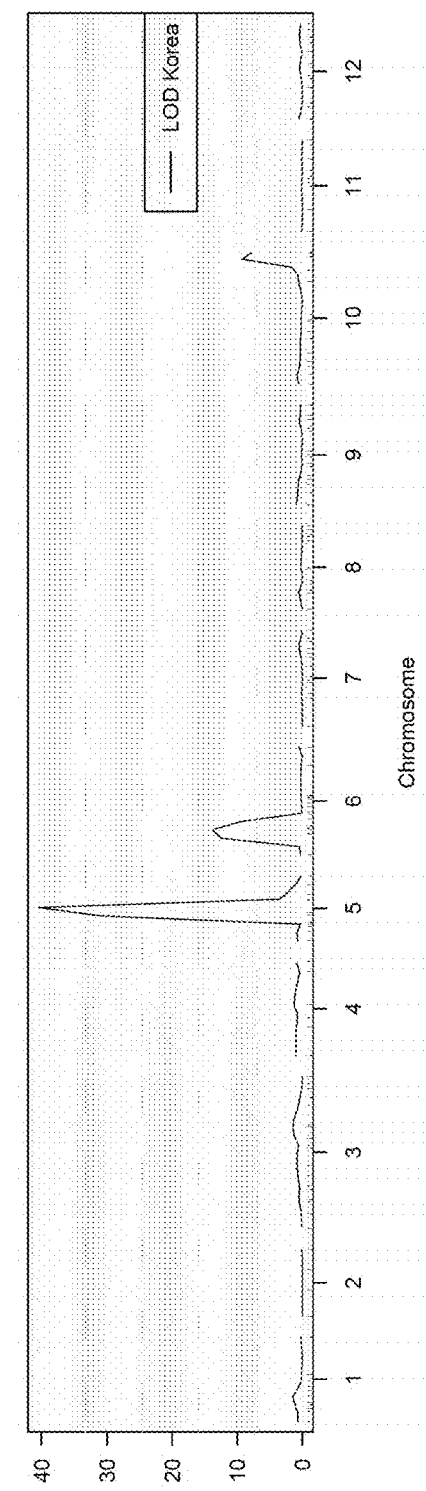
FIG. 1: Shows *Phytophthora capsici* resistance QTL LOD scores based on analysis of the mapping population.

*Phytophthora capsici* L. (*P. capsici*) is an oomycete and soil-born pathogen that causes root rot in pepper (*Capsicum annuum*) and is therefore a major threat for pepper production worldwide. *P. capsici* is extremely difficult to eradicate. In the past, soil treatments using methyl bromide were used to control the disease. However, the polluting nature of this compound has led to bans on its use in many areas of the developed world. There is therefore a great need for development of *P. capsici* resistant plants to offset the pepper production loss as a result of root rot.

'Criollo de Morelos 334 (CM334)' is a Mexican landrace of *Capsicum annuum* that shows the strongest resistance against *P. capsici*. A QTL on chromosome 5 was eventually identified as the major effect locus for *P. capsici* resistance, but this locus provides only partial resistance that is quantitative and inconsistent under high disease pressure. Thus, the resistance derived from this locus has been insufficient.

Additionally, introgression of the *P. capsici* resistance locus on chromosome 5 into commercial pepper lines results in progeny plants bearing fruit with undesirable characteristics. CM334 plants produce small, pungent, elongated fruit, such that when CM334 is crossed with other pepper types, such as bell peppers, the progeny plants produce fruit that are elongated in shape rather than the desirable blocky shape. While fruit shape loci associated with the *P. capsici* resistance locus have been identified and methods to break this linkage are described in, for example, WO2012076980A1, the phenotype of such fruit has been deficient, particularly with regard to immature fruit color.

Crosses between line CM334 and bell pepper lines have therefore previously resulted in fruit that was light green at the immature stage. This phenotype is undesirable to breeders in the commercial production of green bell peppers. This type of pepper is typically harvested at the immature stage when the fruit are dark green in color. Additionally, consumers preferentially buy darker green bell peppers due to the perception that the color is associated with higher quality and nutritional benefits. Thus, the light green immature fruit color phenotype has presented a barrier to developing commercially acceptable bell pepper plants comprising *P. capsici* resistance. Prior to the present disclosure, loci associated with immature fruit color in pepper were identified on chromosome 8 and chromosome 10.

Despite the many obstacles to the successful introgression of *P. capsici* resistance alleles into cultivated pepper lines, the present inventors were able to produce novel introgressions from donor lines that confer *P. capsici* resistance without the undesirable light green immature fruit color trait previously associated such introgressions. In particular, the present invention provides novel trait-linked markers that can be used to make novel recombined introgressions on chromosome 5 and confer *P. capsici* resistance. Surprisingly, the invention was able to provide a chromosomal segment from approximately 39.4 cM to 41.8 cM on chromosome 5 associated with *P. capsici* resistance, but that is not associated with the light green immature fruit color phenotype when recombined and introgressed into cultivated pepper lines.

The invention additionally provides pepper plants comprising novel introgressions from donor lines that confer *P. capsici* resistance without the undesirable light green immature fruit color phenotype previously associated such introgressions, and further comprise a second locus on chromosome 6 that enhances the *P. capsici* resistance conferred by the introgression from chromosome 5. Such plants exhibit improved *P. capsici* resistance under all disease pressures. Specifically, plants comprising both loci were resistant under both low and high disease pressures (exposed to less aggressive and highly aggressive isolates respectively; the same effect is observed using the same isolate, but creating differences in the amount of zoospores in the inoculum, where high disease pressure has around a 100-fold more zoospores in the inoculum) whereas plants comprising only the locus on chromosome 5 were resistant under low disease pressure but susceptible under high disease pressure. The invention therefore provides a chromosomal segment from approximately 26.4 cM to 28.7 cM on chromosome 6 that enhances the *P. capsici* resistance conferred by the locus on chromosome 5.

The invention further provides novel trait-linked markers that allow the accurate identification and tracking of the aforementioned chromosomal regions during plant breeding. In particular embodiments, the invention provides the markers shown in Table 1, including markers within a chromosomal segment flanked by marker loci SNPmarker_7 and SNPmarker_12 on chromosome 5. Other embodiments of the invention provide novel markers SNPmarker_8, SNPmarker_9, SNPmarker_10, SNPmarker_11, and SNPmarker_21, which are useful in detection and tracking of plants comprising a small *P. capsici* resistance locus on chromosome 5 but lacking the light green immature fruit color phenotype during plant breeding. Marker status for *P. capsici* resistance donor (CM334) and *P. capsici* susceptible parent (SBR-99-1274), as well as plants comprising the recombinant introgression on chromosome 5, is shown in Table 1. In certain embodiments, the invention provides the markers shown in FIG. 3, including markers within a chromosomal segment flanked by marker loci SNPmarker_1 or SNPmarker_2, which are useful in detection and tracking of plants comprising the *P. capsici* resistance-enhancing locus on chromosome 6.

I. Genomic Regions, Alleles, and Polymorphisms Associated with *P. capsici* Resistance in Pepper Plants

*P. capsici* can infect pepper plants at any stage in the growth cycle and can cause severe reduction in yield and quality in a pepper crop. Cultivar resistance is the most economically feasible way of controlling *P. capsici* infection due the high cost of fungicide applications and environmental and health risks associated with the use of such chemicals. Intensive efforts have therefore been made to identify effective sources of *P. capsici* resistance. However, previously known introgressions from *P. capsici* resistant accessions confer only a partial resistance while also being associated with commercially unacceptable fruit traits.

CM334 is the original source for *P. capsici* resistance on chromosome 5 in pepper and is widely used in the industry. Other sources of *P. capsici* resistance on chromosome 5 are known in the art and include PI201234, Aristotle, Archimedes, Turnpike, and Paladin. Archimedes, Turnpike, and Paladin can also be used as sources for the resistance enhancement locus on chromosome 6.

The locus on chromosome 5 that confers *P. capsici* resistance has been introduced into commercial pepper varieties, but the resistance exhibited by these plants is variable based on the genotype of the plants and level of disease pressure. The present inventors surprisingly found that a locus on chromosome 6 stabilizes the resistance conferred by the locus on chromosome 5. Plants comprising both loci consistently exhibited improved resistance under low and high disease pressure compared to plants comprising only the resistance locus on chromosome 5. Furthermore, this improved resistance was observed in *C. annuum* plants with different genetic backgrounds. Interestingly, the locus on chromosome 6 did not provide a resistant phenotype on its own. Given that the chromosome 6 locus does not provide a distinct selectable phenotype other than when it is present in combination with the locus on chromosome 5, the development of markers to select for plants comprising the locus on chromosome 6 by the inventors was particularly significant. The present invention therefore provides for cultivated pepper plants that exhibit improved *P. capsici* resistance under all levels of disease pressure, but do not produce light green immature fruit.

In certain embodiments, the invention therefore provides pepper plants comprising donor DNA from a *P. capsici* resistant line that maps between approximately 39.4 cM and 41.8 cM on chromosome 5. In other embodiments, the invention provides plants comprising introgressions mapped between about 26.4 cM and 28.7 cM on chromosome 6. When both novel introgressions are present, they provide resistance to *P. capsici* under all levels of disease pressure, while avoiding the light green immature fruit color phenotype associated with conventional introgressions.

Other embodiments of the invention provide novel markers for the selection of the chromosome 5 and 6 loci. Examples of such markers include SNPmarker_7, SNPmarker_8, SNPmarker_9, SNPmarker_10, SNPmarker_11, SNPmarker_12, SNPmarker_1, and SNPmarker_2, which have been shown to be genetically linked to *P. capsici* resistance in plants.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions disclosed herein from a *P. capsici* resistant plant into a cultivated line. The invention further provides markers for identifying and tracking the novel introgressions disclosed herein during plant breeding, such as markers SNPmarker_7, SNPmarker_8, SNPmarker_9, SNPmarker_10, SNPmarker_11, SNPmarker_12, SNPmarker_1, SNPmarker_2, and SNPmarker_21.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistance phenotype.

Pepper plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for disease resistance introgression are also provided. Pepper plants comprising an introgressed region closely linked to, or adjacent to, the genomic regions and markers provided herein and associated with a disease resistance phenotype are also provided.

III. Development of Disease Resistant Pepper Varieties

For most breeding objectives, commercial breeders work within germplasm that is "cultivated," "cultivated type," or "elite." As used herein, "elite" or "cultivated" variety means a variety that has resulted from breeding and selection for superior horticultural performance for use in agriculture.

This germplasm is easier to breed because it generally performs well when evaluated for horticultural performance. A number of cultivated pepper types have been developed, which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach generally presents significant difficulties due to fertility problems associated with crosses between diverse lines, and negative linkage drag from the non-cultivated parent. For example, non-cultivated pepper lines can provide alleles associated with disease resistance. However, these non-cultivated lines may have poor horticultural qualities such as undesirable fruit shape, undesirable immature fruit color, small fruit size, or low yield.

The process of introgressing desirable resistance genes from non-cultivated lines into elite cultivated lines while avoiding problems with linkage drag or low heritability of the desired trait in crosses with the non-cultivated lines is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance will facilitate the development of pepper plants having beneficial phenotypes. For example, seed can be genotyped using the markers of the present invention in order to select for plants comprising desired genomic regions associated with disease resistance, without the need for growing plants to maturity to evaluate the phenotype. Moreover, MAS allows identification of plants homozygous or heterozygous for a desired introgression.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp 1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit resistance to *P. capsici*. Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics,* 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a pepper plant a genotype associated with disease resistance, identify a pepper plant with a genotype associated with disease resistance, and to select a pepper plant with a genotype associated with disease resistance. In certain embodiments of methods of the invention, polymorphic nucleic acids can be used to produce a pepper plant that comprises in its genome an introgressed locus associated with disease resistance. In certain embodiments of the invention, polymorphic nucleic acids can be used to breed progeny pepper plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in pepper plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat.

No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which pepper plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of pepper breeding. An "elite population" is an assortment of elite individuals or varieties that can be used to represent the state of the art in terms of agronomically superior genotypes of a given crop species, such as pepper. Similarly, an "elite germplasm" or elite strain of germplasm is an agronomically superior germplasm.

As used herein, the term "introgressed" or "introgression," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked" or "genetically linked," when used in the context of nucleic acid markers and/or genomic regions, means that the markers and/or genomic regions are located in proximity on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to *P. capsici*.

As used herein, "resistance allele" means the nucleic acid sequence associated with resistance or tolerance to disease.

As used herein, "resistance" or "improved resistance" in a plant to disease conditions is an indication that the plant is more able to reduce disease burden than a non-resistant or less-resistant plant. Resistance is a relative term, indicating that a "resistant" plant is more able to reduce disease burden compared to a different (less resistant) plant (e.g. a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistance."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

V. Deposit Information

A deposit was made of at least 2500 seeds of pepper line SBRHJ12-G011, which comprises a reduced introgression, as described herein. The deposit was made with the American Type Culture Collection (ATCC), 10801 University Boulevard, Manassas, Va. 20110-2209 USA. The deposit is assigned ATCC Accession No. PTA-123693, and the date of deposit was Nov. 14, 2016. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1

Identification of Immature Fruit Color Locus on Chromosome 5

The undesirable light green immature fruit color phenotype associated with the introgression of the *P. capsici* resistance locus on chromosome 5 from CM334 was first observed in an ancho hybrid comprising the introgression. Using earlier backcross generations from this conversion, the light green immature fruit color phenotype was found to be associated with a locus approximately 20 cM upstream of the *P. capsici* resistance locus on chromosome 5. The light green immature fruit color locus on chromosome 5 was later mapped and validated in an unrelated $F_3$ population derived from a cross between the blocky line SBY-99-1160 and the ancho line HAP-114-1005. Fine mapping in a backcross population derived from a cross between CM334 and the ancho line HAP-114-1005 further refined the light green immature fruit color locus to a 3 cM region on chromosome 5 and subsequent SNP association within this region culminated in the development of the trait linked marker SNPmarker_21. The light green immature fruit color phenotype was later observed in multiple trials for several blocky hybrids comprising the *P. capsici* resistance locus on chromosome 5 from CM334. Fingerprint analysis of these blocky hybrids indicated that the introgression from CM334 on chromosome 5 encompassed the previously identified light green immature fruit color locus.

Example 2

Identification of *P. capsici* Resistance-Enhancing Locus on Chromosome 6

A doubled haploid (DH) population was generated to identify additional loci associated with *P. capsici* resistance. A DH population consisting of 181 lines was developed from the $F_1$ progeny generated from the cross between the resistant hot pepper line HAS-144-6103 and the susceptible hot pepper line HAS-144-1357. Greenhouse assays were performed to evaluate symptom severity of lines under high disease pressure and low disease pressure. In one assay, disease pressure was determined by isolate concentration, wherein high disease pressure was induced by inoculating seedlings with a *P. capsici* isolate at a concentration of $1\times10^6$/mL zoospores, whereas a concentration of $1\times10^4$/mL zoospores of the same *P. capsici* isolate was used to induce low disease pressure. In another assay, high disease pressure was induced by inoculating seedlings with a more virulent *P. capsici* isolate. Seedlings were inoculated between the 4-7 leaf stage and infection symptoms were evaluated 8-10 days post inoculation. Seedlings were scored on a scale of 1-9, where 1=no symptoms; 3=small lesions at the base of the stem; 5=dark brown lesions at the base of the stem but not growing upward; 7=large brown lesions growing upward, plant wilting; and 9=death. It was observed that both assays resulted in similar experimental outcomes.

Figure 2:
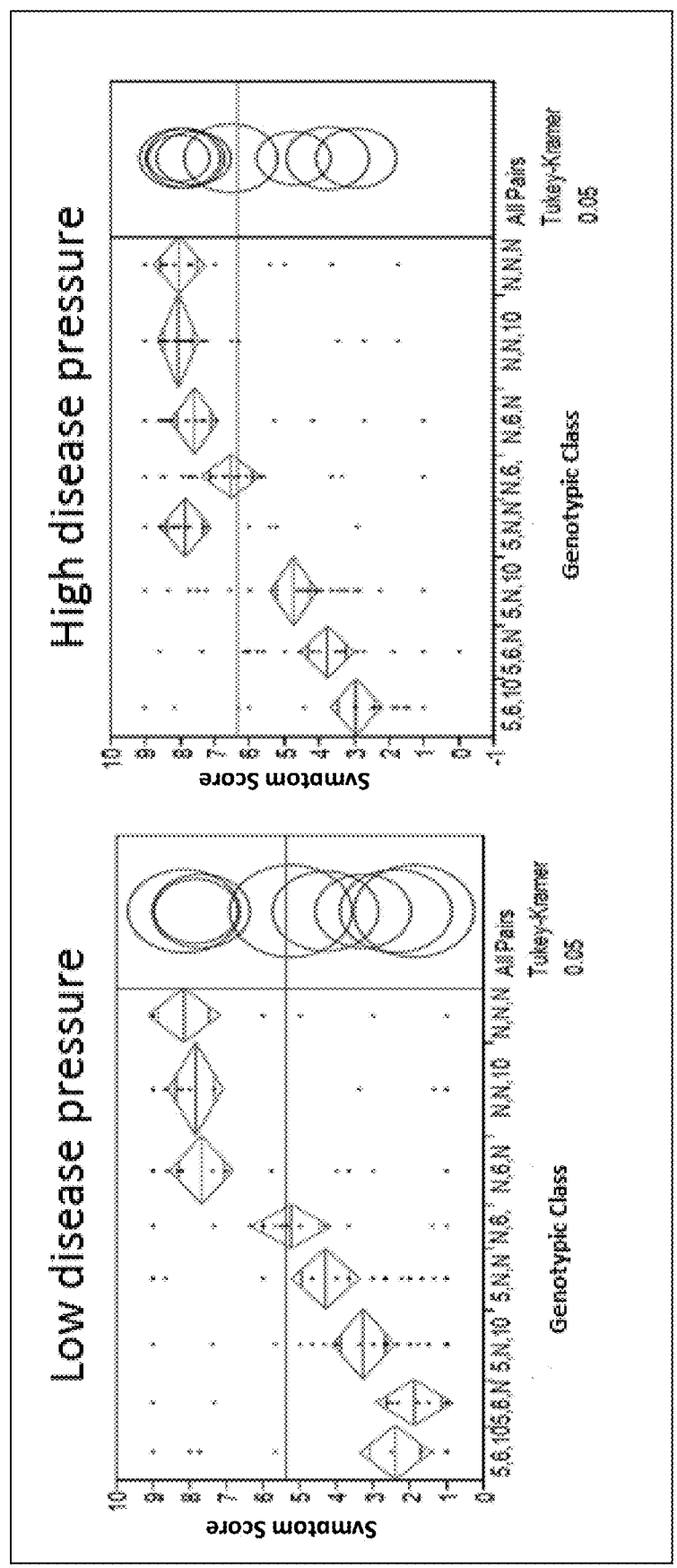
FIG. 2: Shows efficacy data of the loci on chromosome 5 and chromosome 6 in all possible genetic combinations under high and low disease pressure.
Figure 3:
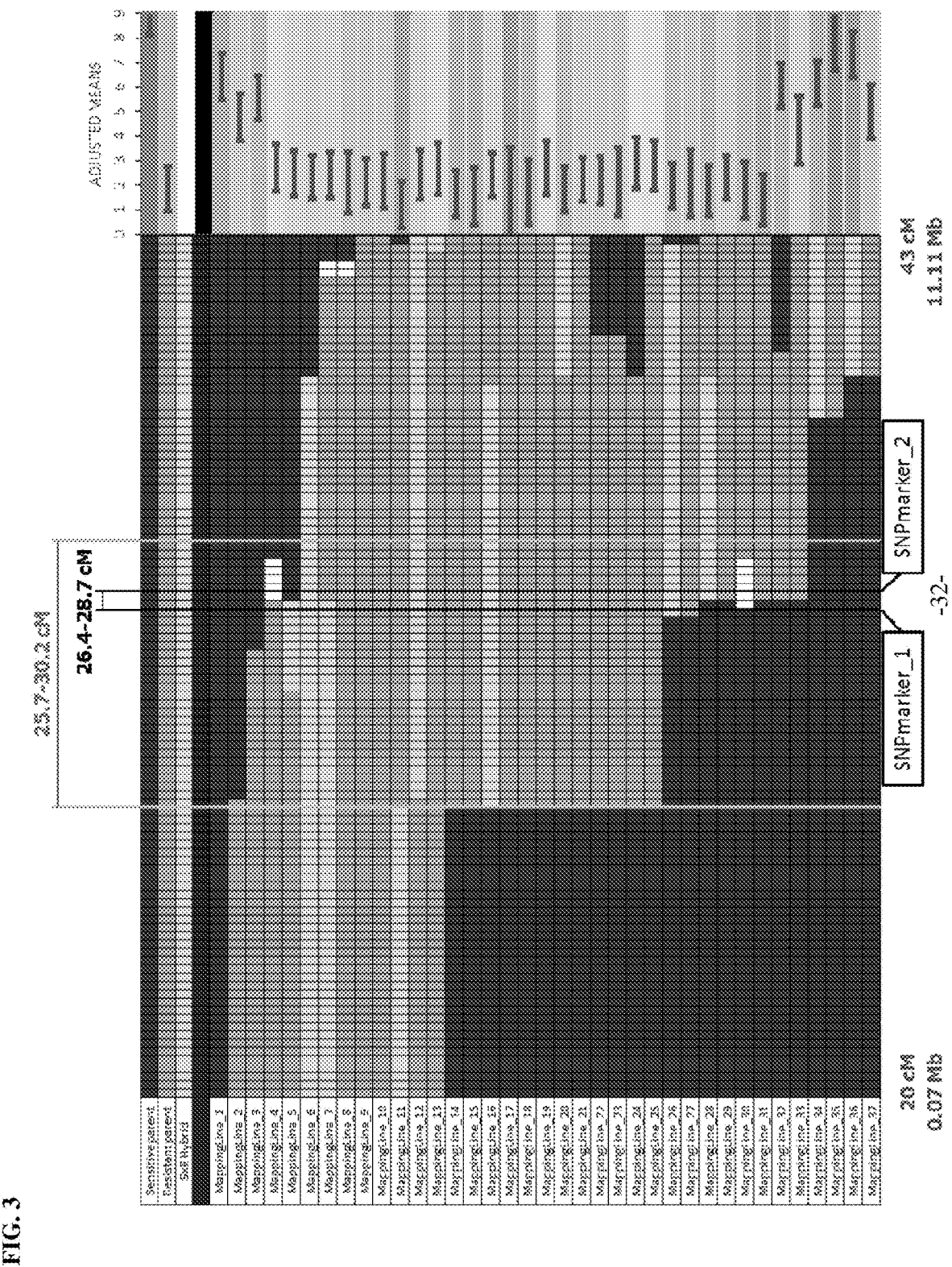
FIG. 3: Shows the boundaries of the *P. capsici* resistance-enhancing locus on chromosome 6, determined through fine mapping.

Composite interval mapping using disease severity data from these greenhouse assays identified the QTL on chromosome 5, as well as a smaller effect QTL on chromosome 6 and chromosome 10 (FIG. 1). Adjusted marginal means (least squares means) and confidence intervals from a general linear model were estimated for each combined genotypic class across the loci on chromosomes 5, 6 and 10. These marginal means indicated that the locus on chromosome 6 on its own had no effect on the severity of disease symptoms (FIG. 2). However, DH lines comprising the locus on chromosome 5 as well as the locus on chromosome 6 surprisingly showed significantly reduced symptoms compared to DH lines comprising only the locus on chromosome 5. Under high disease pressure conditions, lines fixed for resistance at the locus on chromosome 5 alone were fully susceptible (not significantly different from the fully susceptible genotypic class), whereas lines fixed for resistance at both the locus on chromosome 5 and the locus on chromosome 6 had significantly reduced symptoms (FIG. 2). It was concluded that the locus on chromosome 6 acts epistatically to modify the effect of the primary resistance locus on chromosome 5.

Example 3

Development of Trait Linked Markers

Using the trait marker SNPmarker_7 and the trait marker SNPmarker_21, it was possible to break the linkage between the light green immature fruit color phenotype and *P. capsici* resistance. Through backcrossing and recombinant selection, a small (2 cM) efficacious introgression of the *P. capsici* resistance locus on chromosome 5 from CM334 was developed in a blocky pepper line. This recombination event is defined by markers SNPmarker_7 at 39.4 cM and by SNPmarker_12 at 41.8 cM. Markers that are capable of differentiating this breeding event from all other resistant *P. capsici* resistant lines have been developed and are shown in Table 1.

TABLE 1

Marker status for *P. capsici* resistance donor (CM334) and *P. capsici* susceptible parent (SBR-99-1274), as well as a resistant hybrid plant comprising the recombinant introgression on chromosome 5 (SBRHJ12-G011).

| Marker | Position (cM) | Alleles | CM334 | SBR-99-1274 | SBRHJ12-G011 |
|---|---|---|---|---|---|
| SNPmarker_3 | 30.7952053 | G/T | GG | TT | TT |
| SNPmarker_4 | 34.97934691 | C/T | CC | TT | TT |
| SNPmarker_5 | 36.63826809 | C/T | TT | CC | CC |
| SNPmarker_6 | 36.63826809 | C/G | CC | GG | GG |
| SNPmarker_7 | 39.36098489 | A/G | AA | GG | GG |
| SNPmarker_8 | 39.4 | C/T | TT | CC | CC |
| SNPmarker_9 | 39.4 | G/T | GG | TT | TT |
| SNPmarker_10 | 39.4 | G/T | GG | TT | TT |
| SNPmarker_11 | 40.8 | A/T | TT | AA | TT |
| SNPmarker_12 | 41.7523237 | A/T | AA | TT | TT |
| SNPmarker_13 | 55.03140844 | C/T | TT | CC | CC |
| SNPmarker_14 | 55.03140844 | C/G | CC | GG | GG |
| SNPmarker_15 | 55.03140844 | A/G | AA | GG | GG |
| SNPmarker_16 | 55.03140844 | A/G | AA | GG | GG |
| SNPmarker_17 | 55.03140844 | G/T | GG | TT | TT |
| SNPmarker_18 | 55.06628311 | C/G | CC | GG | GG |
| SNPmarker_19 | 55.06628311 | C/T | TT | CC | CC |
| SNPmarker_20 | 55.06628311 | A/T | AA | TT | TT |

Blocky pepper lines carrying this introgression, such as pepper line SBRHJ12-G011, do not produce light green fruit at the immature stage. The recombination event has been placed into several elite blocky breeding lines using marker assisted backcrossing and are being evaluated for equivalency to the recurrent parent.

Example 4

Identification of AIG1 as the Gene for *P. capsici* Resistance

Figure 4:
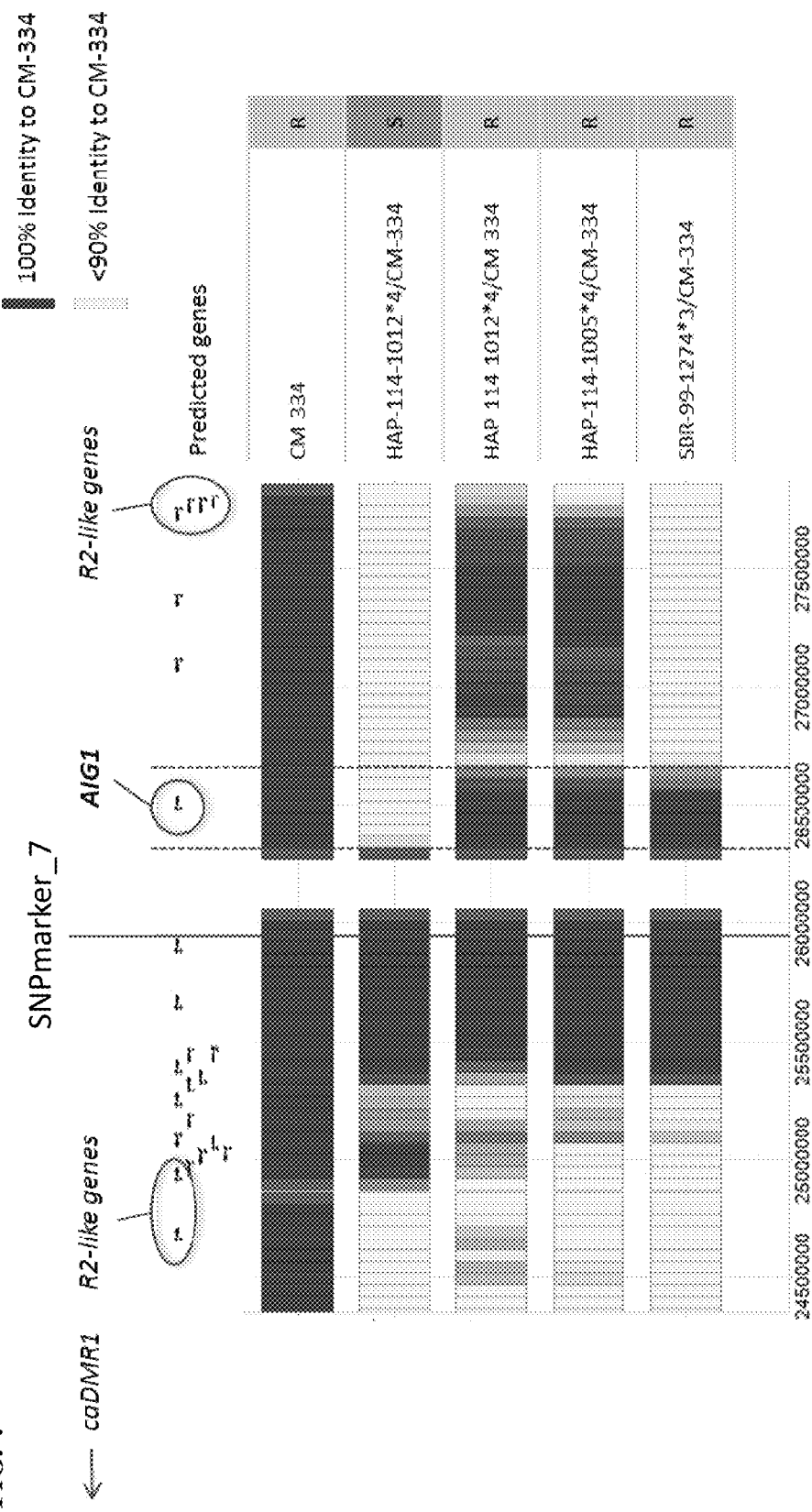
FIG. 4: Shows mapping results implicating AIG1 as the gene for *P. capsici* resistance on chromosome 5.

The locus on chromosome 5 from CM334 conferring resistance to *P. capsici* was introgressed into a large number of pepper breeding lines through several generations of backcrossing with foreground marker assisted selection for resistance. The marker being used for foreground selection has near perfect association with resistance across numerous germplasm. One conversion of the ancho line HAP-114-1012 was identified as comprising a small introgression around the trait linked marker, but demonstrated no resistance in pathology assays. Larger introgressions of this trait into HAP-114-1012 within sister lines did show resistance. The non-efficacious conversion was sequence captured along with several efficacious conversions with the intention of defining recombination breakpoints with high resolution and further fine mapping of the *P. capsici* resistance locus on chromosome 5. The percent identity of each line to CM334 within the trait region based on the sequence capture data is shown below. Using the recombination breakpoints elucidated by sequence capture, it was possible to delineate the *P. capsici* resistance trait region to a narrow interval that encompassed only a single predicted gene, AIG1 (FIG. 4). AIG1 is a known disease resistance gene in *Arabidopsis*. This narrow trait interval provided strong evidence to conclude that caDMR1 and the R2-like genes, while tightly linked to resistance, are not the primary determinant of resistance to *P. capsici* in pepper.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A pepper plant of a cultivated pepper variety comprising a recombinant introgression on chromosome 5 that comprises a first allele conferring resistance to *Phytophthora capsici*, wherein said recombinant introgression is flanked in the genome of said plant by marker locus SNPmarker_7 (SEQ ID NO: 1) and marker locus SNPmarker_12 (SEQ ID NO: 6), wherein said first allele lacks a second allele genetically linked thereto that confers a light green immature fruit color phenotype when present, and wherein a representative sample of seed comprising said allele conferring resistance to *Phytophthora capsici* has been deposited under ATCC Accession No. PTA-123693.

2. The pepper plant of claim 1, wherein said recombinant introgression is located between about 39.4 cM and about 41.8 cM on chromosome 5 of said plant.

3. The pepper plant of claim 1, wherein said recombinant introgression comprises the gene AIG1 on chromosome 5 of said plant.

4. The pepper plant of claim 1, wherein a representative sample of seed comprising said recombinant introgression has been deposited under ATCC Accession No. PTA-123693.

5. A plant part of the pepper plant of claim 1.

6. The plant part of claim 5, wherein said plant part is a cell, a seed, a root, a stem, a leaf, a fruit, a flower, or pollen.

7. The plant of claim 1, further comprising an introgressed chromosomal segment from chromosome 6 of a donor pepper plant, wherein said chromosomal segment confers improved *Phytophthora capsici* resistance under all disease pressures relative to a plant lacking said chromosomal segment.

8. The pepper plant of claim 7, wherein said chromosomal segment is associated with (selected by) marker locus SNPmarker_1 (SEQ ID NO: 8) or marker locus SNPmarker_2 (SEQ ID NO: 9).

9. The pepper plant of claim 8, wherein said chromosomal segment is located between about 26.4 cM and about 28.7 cM on chromosome 6.

10. A method for producing a pepper plant exhibiting resistance to *Phytophthora capsici* comprising:
    a) crossing the pepper plant of claim 1 with itself or with a second pepper plant of a different genotype to produce one or more progeny plants; and
    b) selecting a progeny plant comprising said recombinant introgression.

11. The method of claim 10, wherein selecting said progeny plant comprises identifying a genetic marker genetically linked to said recombinant introgression.

12. The method of claim 11, wherein selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), and SNPmarker_21 (SEQ ID NO: 7).

13. The method of claim 12, wherein selecting a progeny plant comprises detecting a polymorphism at locus SNPmarker_8 (SEQ ID NO: 2) and a polymorphism at locus SNPmarker_21 (SEQ ID NO: 7).

14. The method of claim 10, wherein said progeny plant is an $F_2$-$F_6$ progeny plant.

15. The method of claim 10, wherein producing said progeny plant comprises backcrossing.

16. The method of claim 15, wherein backcrossing comprises from 2-7 generations of backcrossing.

17. A method for obtaining a pepper plant of a cultivated variety exhibiting resistance to *Phytophthora capsici* comprising:
    a) obtaining a pepper plant of a cultivated variety that is heterozygous for a first allele from a donor parent that confers resistance to *Phytophthora capsici* that is genetically linked to a second allele that confers a light green immature fruit color phenotype;
    b) obtaining progeny of the plant; and
    c) selecting at least a first progeny plant in which recombination has occurred such that the progeny comprises said first allele that confers resistance to *Phytophthora capsici* and lacks said second allele that confers a light green immature fruit color phenotype;

wherein a representative sample of seed comprising said allele that confers resistance to *Phytophthora capsici* has been deposited under ATCC Accession No. PTA-123693.

18. The method of claim 17, wherein selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), and SNPmarker_21 (SEQ ID NO: 7).

19. The method of claim 18, wherein selecting a progeny plant further comprises detecting a polymorphism at locus SNPmarker_8 (SEQ ID NO: 2) and a polymorphism at locus SNPmarker_21 (SEQ ID NO: 7).

20. A plant produced by the method of claim 17.

21. A part of the plant of claim 20, selected from the group consisting of a cell, a seed, a root, a stem, a leaf, a fruit, a flower, and pollen.

22. A method for producing a pepper plant exhibiting improved *Phytophthora capsici* resistance under all disease pressures comprising:
    a) crossing the pepper plant of claim 8 with itself or with a second pepper plant of a different genotype to produce one or more progeny plants; and
    b) selecting a progeny plant comprising said recombinant introgression and said introgressed chromosomal segment.

23. The method of claim 22, wherein selecting the progeny plant comprises 1) identifying a genetic marker genetically linked to said recombinant introgression; and 2) identifying a genetic marker genetically linked to said introgressed chromosomal segment.

24. The method of claim 23, wherein selecting a progeny plant comprises detecting at least one polymorphism at a locus selected from the group consisting of SNPmarker_7 (SEQ ID NO: 1), SNPmarker_8 (SEQ ID NO: 2), SNPmarker_9 (SEQ ID NO: 3), SNPmarker_10 (SEQ ID NO: 4), SNPmarker_11 (SEQ ID NO: 5), SNPmarker_12 (SEQ ID NO: 6), SNPmarker_21 (SEQ ID NO: 7), SNPmarker_1 (SEQ ID NO: 8), and SNPmarker_2 (SEQ ID NO: 9).

25. The method of claim 24, wherein selecting a progeny plant further comprises detecting a polymorphism at locus SNPmarker_8 (SEQ ID NO: 2), a polymorphism at locus SNPmarker_21 (SEQ ID NO: 7), a polymorphism at locus SNPmarker_1 (SEQ ID NO: 8), and a polymorphism at locus SNPmarker_2 (SEQ ID NO: 9).

26. The method of claim 22, wherein said progeny plant is an $F_2$-$F_6$ progeny plant.

27. The method of claim 22, wherein producing said progeny plant comprises backcrossing.

28. The method of claim 27, wherein backcrossing comprises from 2-7 generations of backcrossing.

* * * * *

SEQUENCE LISTING

```
<160> NUMBER OF SEQ ID NOS: 9

<210> SEQ ID NO 1
<211> LENGTH: 940
<212> TYPE: DNA
<213> ORGANISM: Capsicum annuum

<400> SEQUENCE: 1
gcagctgcag ttccaggtat gaatgagttc aaccctgtgg acaccagagg aggaggaggt      60
tgtaatgatg ctgcaggaga tacattcttt acatccacag aatgatcagg agcagcaggc     120
tgccacaaac aaataggtct tgtcagacac gcaccaatgc cagcaaaagg aaaactttaa     180
aaacgaaaaa aacaccctct gaaagacaca taggagaacc ctaggaaaat ccatgaataa     240
aattttcata attagttgga aggtcaattg ccgcaaatga tgactrggac ttcctaaaca     300
agattaagac ttcatcaatg caatatccca aatacaacag tgcaaccctc acacttgcca     360
```

-continued

```
acagcagcag atgaggggag caaagaataa cagatgattc atagcagccc ttcatagaac    420
accacacaaa aaaacattcc gaaagaaagc aacatattgt ctttagagtt gattgaacag    480
agctgtcaac tgctttaaaa gttaaatcac atatacacat aacttcatac gagaaatcac    540
ttaaacgaac ttactaaaaa ttaactctta aaatatggaa ccagaacagt aaaaagaaaa    600
aagcaaacaa ggacttctag tattcaggaa ctgttaaatc ctatcttctt gtgggatttc    660
actgggtatg ttgttgttgt tgttgttgtt aagcgatgaa taaattaaa tgcaaaacca    720 ataagtacct ttatgtagat tagaaatctt taagtgtcct agtaaagttt ctaactttcc    780
atgtaatttg atatttgata atagacaaca cttatgctct tcctgaactg tacgatgcaa    840
ttttaaccaa atgaaacccc aggtaacaat gcaaagggta tctaggacca attcccaaaa    900
cttgtcaatt attcaatcct gtaaaaagaa ggatctccac                          940
```

```
<210> SEQ ID NO 2
<211> LENGTH: 301
<212> TYPE: DNA
<213> ORGANISM: Capsicum annuum
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (181)..(182)
<223> OTHER INFORMATION: n is a, c, g, or t

<400> SEQUENCE: 2
taatttgata tttgataata gacaacactt atgctcttcc tgaactgtac gatgcnattt     60
taaccaaatg aaaccccagg taacantgca aagggtatct aggaccaatt cccaaaactt    120
gtcaattatt cantcctgta aaagaagga yctccactgc agtatttacc actgtcttcc    180 nncctagca taccttcaaa atattgtttt cctgtatgg acttaaagca cacatcctac     240
acaacatgtt cttcacaatc ctacatacta tgattttagc caactttact tactctaact    300
c                                                                    301
```

```
<210> SEQ ID NO 3
<211> LENGTH: 301
<212> TYPE: DNA
<213> ORGANISM: Capsicum annuum
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
```

```
<220> FEATURE:
<221> NAME/KEY: misc_feature
<222> LOCATION: (184)..(184)
<223> OTHER INFORMATION: n is a, c, g, or t

<400> SEQUENCE: 3
gtgtcaaaaa aaaatggctg aattgatcct tgacaggtga aaacanacaa attaacggga      60
acaaaaagtg gtattacgtc ncagttgaga ttgaaccatg gtctccaagg tttgcaccca     120
cttcattgac caccngggca cantaccagt kcactatatt ggccccattt ttttccacta     180
ctanacaatt agaaattact tgtgtcactt tcattaatag catgcatata gctgagaacc     240
ataaatgcat atggcttaga tatgcaacat aaagcatgta aaataaaaca aagacgtggc     300
t                                                                    301

<210> SEQ ID NO 4
<211> LENGTH: 301
<212> TYPE: DNA
<213> ORGANISM: Capsicum annuum
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t

<400> SEQUENCE: 4
tacaaaatga agctccaagt ctgatatgta attcctcagt ccctcttttt cctctctatc      60
aactnganaa atgctgtgaa tttaaattta cagttccata tctaatattt tattcctccg     120
agtccgaatt agtttggncc gaatacagca kttcaagaga ttcnttccat tctatttagn     180
ttttatcttt atattttang tntatgaatt ggtattataa attactccta tcatgtccat     240
tagggaaaca gctgggagat gcaacatana gtagagaaat aacaacctga gttgtgttta     300
g                                                                    301

<210> SEQ ID NO 5
<211> LENGTH: 114
<212> TYPE: DNA
<213> ORGANISM: Capsicum annuum
```

<400> SEQUENCE: 5
tcgggctgac aaatgccta gaagccttta tagacttgat gaatagagtg twcaaatagt    60
atttggacat gttgttcata gtctttatca atgatattct tatctattat cata          114

<210> SEQ ID NO 6
<211> LENGTH: 445
<212> TYPE: DNA
<213> ORGANISM: Capsicum annuum

<400> SEQUENCE: 6
acctgtcagg atcaattcag ccatttttt ttgtacactg gttcttttt ttgaaactga     60 caatttggtc gattttatgt gtgagccaca tctaatttct ctttgagaat atgttttag    120 agagttggga acttcctgga aaccattgca agctgcatac cactgcattt caaaatgttc    180
tgtaaaataa tatgaactag tttaactcta gggaaccaaa agcaaccatc accctgcagc    240
agagggagtg tcttctwaag tggatatgta tttcctttgt cattgcatcc cattatgata    300
gaagaccttc ttaatctttt cctgtaactt ttctctctct ctcttaaatt tcaaataaaa    360 caatttttt ttgatactga aaaaactaca agtacatata tttgaaataa aatatgacat    420
gccaaccaaa gggatgcaag caaac                                          445

<210> SEQ ID NO 7
<211> LENGTH: 801
<212> TYPE: DNA
<213> ORGANISM: Capsicum annuum
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (254)..(262)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t

<400> SEQUENCE: 7

```
actaacttt cntttctcat acttcaaata aacacaattt tatcgtttct ccaagatgca      60
ttcattcagt gagtagcatt aaacaataat caaaagttta tcatacaaat gctcaaaaat     120
gggaaaaggt ttaattatct gtcaacaang tccatacact aaaagtctcg ccatgcacag    180
agttcgagaa gtatctacnc acagagtctg ttcacaactt taccatcaat gctangcag     240
ccttaccatn catnnnnnnn nntcagactt atttgcaata atgagaagtt tatcatacaa    300
atgctcaaaa atggaaaaag ggttaaaatt atctgtcaac aaatanaaaa aagtacaggt    360
ccatgcacta aagctctcnt catgcacaga cttcgagaaa rtatctattc acaaaagtct    420
gttgtatgca actttaccat ncatttctgc agctcaacta ctacncatct taccgtgcat    480
ttctgcagct cagacttatt taggccaaac actaacttt tctttctcat acttcaaata    540
aaccgcagca acagcagcaa caaaataaat ctgaataaac acaatagcag gtgtatgata    600
atttatcaca cttttaccag tagcaagttc caccaacaac aatgcagtta atccaagcat    660
agctatcctt ccattaactc tttctgaata ggaactaaac ccgaactcaa cttttagtcc    720
ttcagataca ggttccttta gaggaattgg tggtagaaac acactcgacg accctgatcc    780
tgactcgctc tttctgcctt t                                              801
```

<210> SEQ ID NO 8
<211> LENGTH: 1323
<212> TYPE: DNA
<213> ORGANISM: Capsicum annuum

<400> SEQUENCE: 8

```
ctaaaatttt agcgtatttt tgtcaacctt tttaactgac atagcacctt tttagctaac     60
gtggcacctt tgacgtggcc cccatttta tgtaataaag gtgccacgtc agcacaaaag    120
agtgacaaaa atacgctaaa attgagttcg ggggataata ggaccccgtg aagttggagt    180
gtgtcatagc aactttggtc ataatacaag ggggtacaag atgcttatct cgaagaaaaa    240
tgaaaaatca caagcgcaac gtactttata tgtcagagtg tagcgagtgc acttcaagat    300
gtataataat ttgctcgagg atacagtact aattgaagcg aattacatcg tttcccctat    360
ctatttaata taagaaaggt tttgccgaag aattgggtga aggtgattag acatgacatg    420
acacaacttc aactgaccga ggacatgatc ctatatatga aggcatggag gtcgaggatt    480
agcgtcgaac gttaataggt agacacaagt tgtcatactt ctagtaggat gatttaggta    540
tcacgtagtt tttcccgcct atgttcatta ataactgttg ctatacttgt tttgtgtatt    600
gtttttctgt agtctctctt ttttctctta cttccttgct tttttgcgcc gagggtctat    660
cggaaacaac ctctctaccc cacaaagata gaggtaaggt ctgtttacac tcgatttact    720
gagctcggtc gaggttaagc tgatagctca gaacttgaat gtatattcgt tggtcatart    780
caatctccga accagatcaa cagctccgac accaaggtag ttgagttaag actagcacaa    840
ctttaactaa gctcgcaact tctagtaaag gacgcgtggt tgtgaaacat ggcctgtagg    900
ttctttgttt ttctttgaat aaccgagaaa tatgttgttt ttatcttcaa aactcggtgg    960
atgtttaagc ccctttctc tatcttctc cgtttaaata ccaaacttaa ttcaccgata   1020
gaatttgagc tcatgatgtg cgcctactac acattcttct tctaacaagc atgcgagtga   1080
caggaaaggg cagtaaggaa acaaagaaga tcatatcaaa agaaaatgtg ggcgaacctg   1140
gttgattcct cggtccttt tccagcaatt ttgcccttgg gagccgctga caactgtaaa    1200
gattagaaca cgggatcttc aactcctctc ctccttgtaa gtaagaagac tagttgtttc   1260
```

```
-continued actgtaacta ataatgaaac actaacctgt gaggcaatat cgattccaat ttcatcgagg      1320
acc                                                                    1323

<210> SEQ ID NO 9
<211> LENGTH: 301
<212> TYPE: DNA
<213> ORGANISM: Capsicum annuum
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t

<400> SEQUENCE: 9
taatcctttc tgttcatttc aatgaattag tactctgctt catttggaan atttatccaa        60
ctccattact gtgtatttgc tcattgaaat cgttactgat tttgcttcna ataacataac       120
acgatggaag tcaaggacct atatacatga yaccaactag ttaaggttaa ggcttagtta       180
ttgtttaaac ttacattagc tctggtgcta gctgcttttg gtctagttat tatgttgtgg       240
agctaagtgt gagattcagg aactctagtt tttgaaaacc tttaataccc ccgataattt       300
t                                                                      301
```